US00PP22788P2

(12) United States Plant Patent
Yates

(10) Patent No.: US PP22,788 P2
(45) Date of Patent: Jun. 12, 2012

(54) *BEGONIA* PLANT NAMED 'YAMOUR'

(50) Latin Name: *Begonia boliviensis*
Varietal Denomination: Yamour

(76) Inventor: Frederic C. Yates, Congleton (GB)

( * ) Notice: Subject to any disclaimer, the term of this patent is extended or adjusted under 35 U.S.C. 154(b) by 293 days.

(21) Appl. No.: 12/798,976

(22) Filed: Apr. 15, 2010

(51) Int. Cl.
*A01H 5/00* (2006.01)

(52) U.S. Cl. ..... Plt./343

(58) Field of Classification Search ..... Plt./343
See application file for complete search history.

(56) References Cited

U.S. PATENT DOCUMENTS

PP19,777 P2 * 2/2009 Yates ..... Plt./343
PP19,817 P2 * 3/2009 Yates ..... Plt./343
PP20,093 P3 * 6/2009 Yates ..... Plt./343

OTHER PUBLICATIONS

UPOV ROM GTITM Computer Database, GTI Jouve Retrieval Software 2011/10 Citation for 'YAMOUR'.*

* cited by examiner

*Primary Examiner* — Wendy C Haas
(74) *Attorney, Agent, or Firm* — Penny J. Aguirre

(57) ABSTRACT

A new cultivar of *Begonia boliviensis* named 'YAMOUR', characterized by its semi-pendulous plant habit, its single red flowers, its dark purple-green leaves, its floriferous habit, and its vigorous growth habit.

2 Drawing Sheets

Botanical classification: *Begonia boliviensis.*
Cultivar designation: 'YAMOUR'.

RELATED APPLICATIONS

This application is co-pending with U.S. Plant Patent applications filed for cultivars derived from the same breeding program entitled *Begonia* Plant Named 'YABON' (U.S. Plant patent application Ser. No. 12/799,033), *Begonia* Plant Named 'YAGANCE' (U.S. Plant Pat. No. 19,817), *Begonia* Plant Named 'YAMANCE' (U.S. Plant Pat. No. 19,777), and *Begonia* Plant Named 'YABOS' (U.S. Plant Pat. No. 20,093).

BACKGROUND OF THE INVENTION

The present invention relates to a new and distinct cultivar of *Begonia* plant, botanically known as *Begonia boliviensis* 'YAMOUR' and will be referred to hereafter by its cultivar name, 'YAMOUR'.

The new cultivar was derived from a controlled breeding program conducted by the Inventor at his nursery in Congleton, Cheshire, U.K. The overall purpose of the breeding program established in 2003 is to make selections of *Begonia* plants with compact plant habits suitable for container use combined with superior flower performance and productive stock plants for propagation. 'YAMOUR' was selected in the Inventor's greenhouse in 2006 as a single unique plant from amongst the seedlings derived from a cross made in 2005 between two unnamed, non-commercialized, proprietary parent lines hybrids of *Begonia boliviensis.*

Asexual reproduction of the new cultivar was first accomplished by terminal stem cuttings in Congleton, Cheshire, U.K. in 2007 by the Inventor. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'YAMOUR' as a new and distinct cultivar of *Begonia.*

1. 'YAMOUR' exhibits a semi-pendulous plant habit.
2. 'YAMOUR' exhibits large, single red flowers.
3. 'YAMOUR' exhibits leaves that are dark purple-green leaves.
4. 'YAMOUR' readily produces floriferous side shoots.
5. 'YAMOUR' exhibits a vigorous growth habit.

The parent plants of 'YAMOUR' differ from 'YAMOUR' in that one parent has a large habit with pale red flowers and the other has an upright habit with darker red flowers. 'YAMOUR' can be most closely compared to 'YABOS'. 'YABOS' differs from 'YAMOUR' in having green leaves, shorter internodes, a less vigorous growth habit and smaller red-orange flowers. 'YAMOUR' can also be compared to other cultivars from the same breeding program. 'YAGANCE' differs from 'YAMOUR' in having bicolor pink and white flowers and 'YAMANCE' differs from 'YAMOUR' in having flowers that are pink in color. 'YABON' differs from 'YAMOUR' in having semi-double yellow flowers and a more upright plant habit. 'YAMOUR' can be compared to the cultivar 'Bonfire' (U.S. Plant Pat. No. 15,108). 'Bonfire' differs from 'YAMOUR' in having flowers that are smaller and less red in color.

BRIEF DESCRIPTION OF THE DRAWINGS

The accompanying colored photographs illustrate the overall appearance and distinct characteristics of the new *Begonia*. The photographs were taken in Congleton, Cheshire, U.K. of plants about 6 months in age as grown in a two-liter containers.

Figure 1:
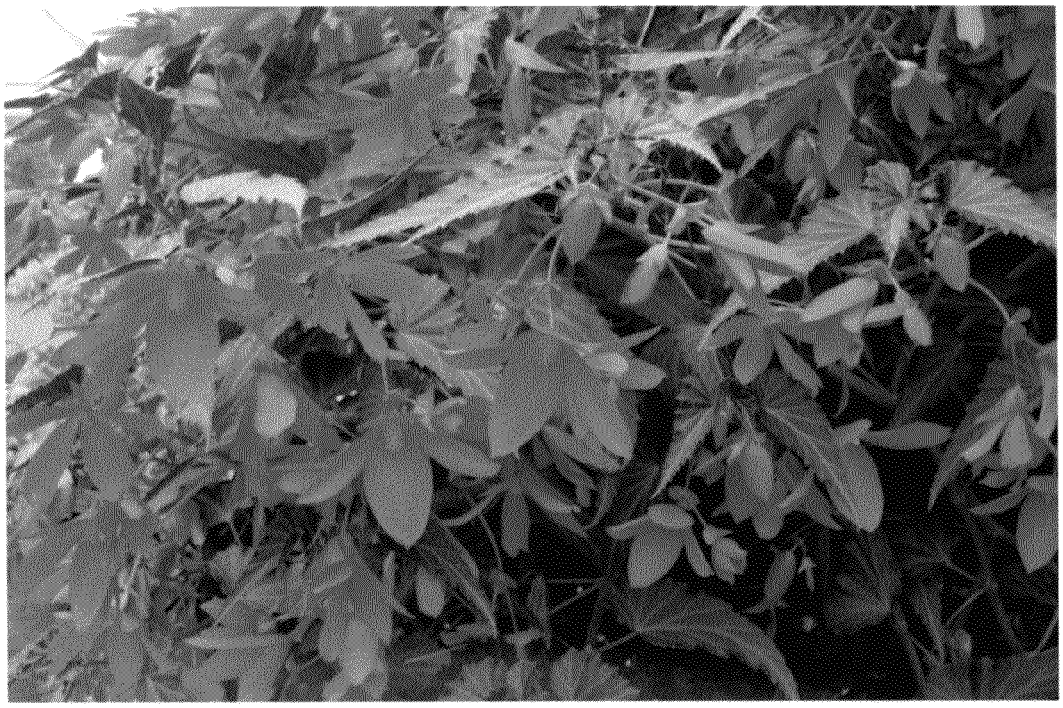
FIG. 1 provides a view of a single plant of 'YAMOUR'.
Figure 2:
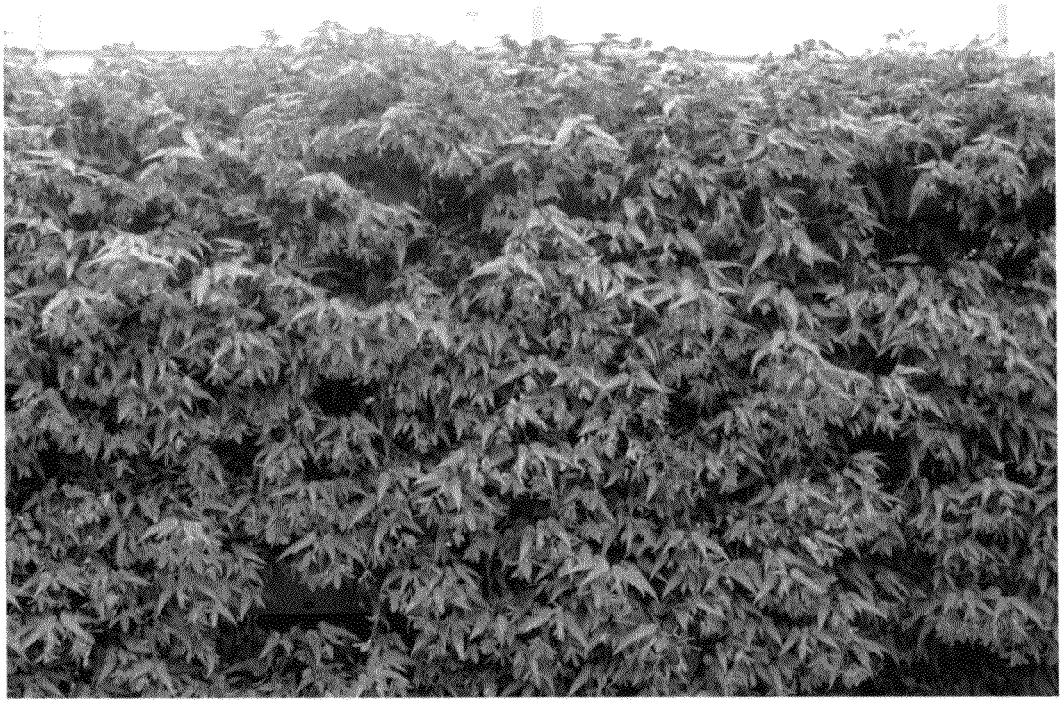

The photograph in FIG. 2 provides a view of a group of plants and illustrates the plant habit and floriferous nature of 'YAMOUR'.

Figure 3:
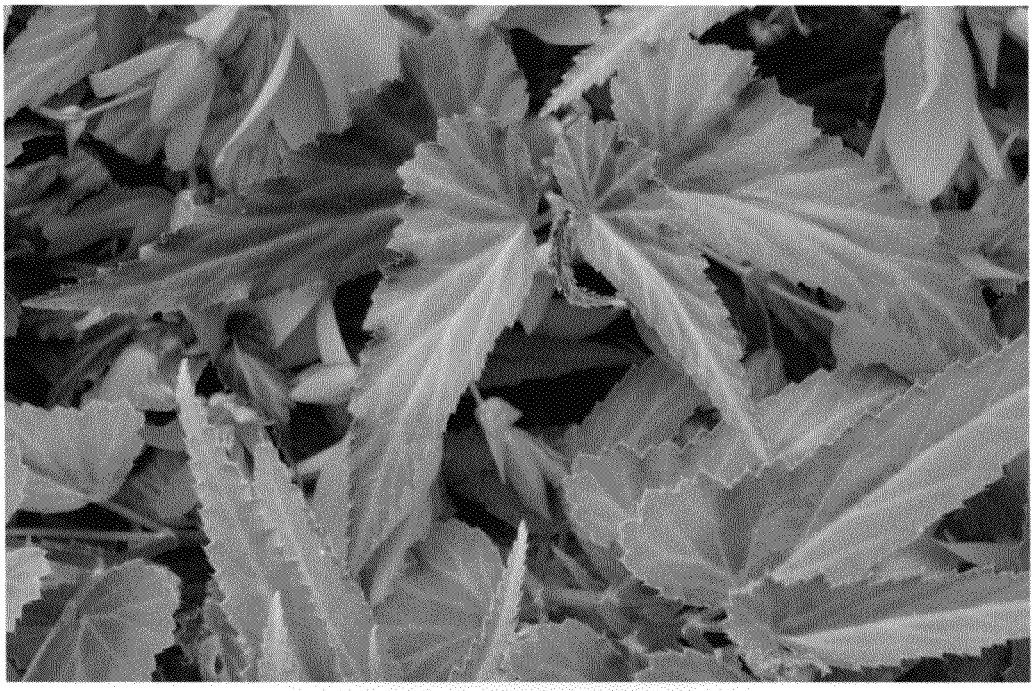

The photograph in FIG. 3 provides a close-up view of the upper leaf surface of 'YAMOUR'.

Figure 4:
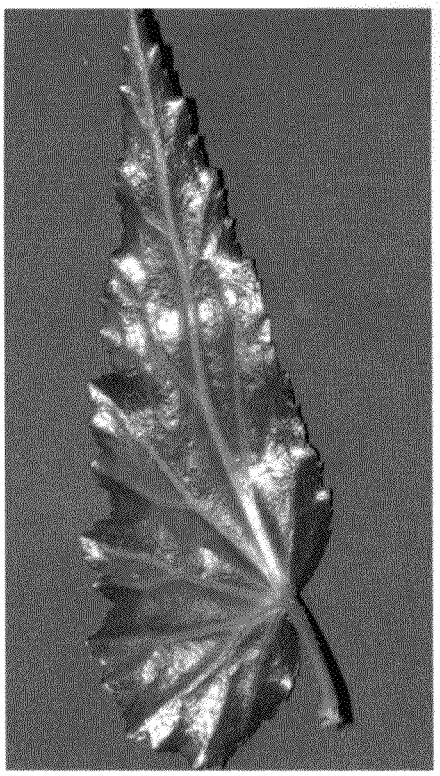

The photograph in FIG. 4 provides a close-up view of the lower leaf surface of 'YAMOUR'.

Figure 5:
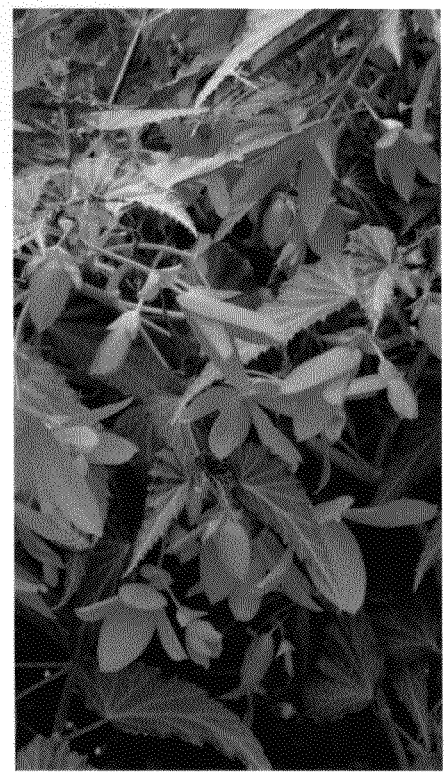

The photograph in FIG. 5 provides a view of the flowers of 'YAMOUR'. The colors in the photograph may differ slightly from the color values cited in the detailed botanical description, which accurately describe the colors of the new *Begonia*.

DETAILED BOTANICAL DESCRIPTION OF THE PLANT

The following is a detailed description of plants of the new cultivar approximately 6 months in age as grown in two-liter containers under greenhouse conditions with ambient light in Congleton, Cheshire, U.K. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General plant characteristics:

*Plant type*.—Deciduous tuberous perennial, grown primarily for use in baskets and containers.

*Plant habit*.—Spreading, well branched, and semi-pendulous (half arching).

*Flowering period*.—From May to October.

*Height and spread*.—Reaches about 45 cm in height and about 40 cm in spread.

*Cold hardiness*.—U.S.D.A. Zone 10.

*Culture*.—Grows in any commercial soil or growing media, 12 hours of light is needed and 20° C. for production in the winter months.

*Diseases and pests*.—No susceptibility or resistance to diseases or pests has been observed.

*Root description*.—Fleshy to fibrous with tubers produced for over-wintering.

*Tubers*.—Slightly flattened, irregularly lobed, slightly depressed in centre, an average of 4 cm in length, 3 cm in height and 2.5 cm in width (larger in older plants), surface is slightly corky, 166C in color with corky patches 177B in color.

Growth and propagation:

*Growth rate*.—Vigorous.

*Propagation*.—Terminal stem cuttings.

*Time required for root initiation*.—7 to 10 days at 20° C.

*Time required for root development*.—5 to 8 weeks to reach commercial size.

Stem description:

*Stem size*.—Average of 2.7 cm in length and 9 mm in width with lateral branches about 5 mm in width.

*Stem shape*.—Round, solid.

*Stem color*.—183C on side exposed to sunlight, 197B on shaded side.

*Stem surface*.—Smooth, glabrous, weakly glaucous, lenticels absent.

*Internode length*.—Average of 7.5 cm.

*Branching habit*.—Freely branched.

*Branching angle at emergence*.—About 60° to horizontal and then becoming pendant.

Foliage description:

*Leaf shape*.—Lanceolate, strongly asymmetric with one side narrowly elliptic, the other narrowly cordate and wider than the other.

*Leaf division*.—Entire.

*Leaf base*.—Weakly cordate.

*Leaf apex*.—Acuminate.

*Leaf venation*.—Pinnate, color 144B on upper surface and 197C on lower surface.

*Leaf margins*.—Irregular serrate with short bristles emerging from tips of the teeth.

*Leaf attachment*.—Petiolate.

*Leaf arrangement*.—Alternate.

*Leaf surface*.—Upper surface; glabrous, lower surface; very weakly pubescent with un-branched translucent straight hairs, lower surface; very glossy.

*Leaf color*.—Upper surface; 200B to N186B and tinged with a color slightly darker than N137A, a 2 to 3 mm band of 144B surrounds veins, lower surface; 183B in color.

*Leaf size*.—Average of 12 cm in length and 3.5 to 4.0 cm in width.

*Leaf quantity*.—Average of 14 per branch.

*Leaf fragrance*.—None.

*Petioles*.—About 2.0 to 3.5 cm in length and 2 mm in width, surface is sparsely pubescent with simple hairs, color is 179A on exposed side and 179D on shaded side.

*Stipules*.—Narrowly triangular in shape, translucent in color and rapidly becoming dry and papery, about 4 mm in length and 2 mm in width, 164B in color.

Flower description:

*Inflorescence type*.—3 (occasionally 2 or 1) flowered cyme produced sequentially in the axils of the upper leaves, monoecious with terminal male flowers developing before the 2 lateral female flowers.

*Peduncles*.—About 4.0 cm in length and 1.5 mm in width, color; 180A on exposed side, 180D on shaded side, surface is glabrous.

*Flower persistence*.—Self-cleaning.

*Flower type*.—Single.

*Flower fragrance*.—None.

*Flower number*.—Average of 10 per inflorescence, one inflorescence per stem.

*Flower aspect*.—Hanging.

*Bracts*.—2, present at base of cyme, broadly ovate in shape, shallowly bifid apex, serrate in upper ¾ of margin, about 9 mm in length and 1.9 cm width, color is in between 179A and 34A.

Male flowers:

*Pedicels*.—About 2.8 cm in length and 1.5 mm in width, color; 41A to 41B on exposed side, 41D on shaded side, glabrous surface.

*Flower buds*.—Flattened ovoid in shape, about 2.7 cm in length and 1.3 cm in width, color is 43B becoming paler towards base.

*Flower size*.—About 4.5 cm in length and 5.0 cm in width.

*Tepals*.—4 in number (2 inner and 2 outer), outer tepals; ovate in shape, acute to obtuse apex, rounded base, average of 5.0 cm in length and 2.3 cm in width, glabrous and smooth surface, entire margin, inner and outer surface 43B in color, glossy at the base on the outer surface.

*Corolla form*.—Flared, tepals are un-fused.

*Stamens*.—Numerous, connate below forming a tube, overall length 1.9 cm, about 5.0 mm in length and 4 mm in width, 11B in color.

*Filaments*.—About 3 mm in length and 0.5 mm in width, 11C in color.

*Anthers*.—Ovate in shape, about 1 mm in length and <1 mm in width, 11C in color.

*Pollen*.—Abundant, 8C in color.

Female flowers:

*Pedicels*.—Average 3.0 cm in length and 1.5 mm in width, 41A to 41B in color on exposed side, 41D in color on shaded side, glabrous surface.

*Flower buds*.—Flattened ovoid in shape, about 2.7 cm in length and 1.3 cm in width, color is 43B becoming paler towards base.

*Flower size*.—About 3.5 cm in length (excluding ovary) and 4.5 cm in width.

*Tepals*.—5 in number (3 inner and 2 outer), outer tepals; narrowly ovate in shape, acute to obtuse apex, rounded base, average of 3.5 cm in length and 1.5 cm in width, glabrous and smooth surface, entire margin, 43C in color, slightly more glossy at base of outer surface, inner tepals; narrowly obelliptic in shape, obtuse apex, narrowly cuneate base, average of 3.4 cm in length and 11 to 14 mm in width, glabrous and smooth surface, entire margin, 43C in color.

*Corolla form*.—Flared, tepals are un-fused.

*Styles*.—3 in number, cylindrical, connate at base for 1 mm, about 3 mm in length and <1 mm in width, 14D in color.

*Stigmas*.—Bifid in shape, stigmatic surfaces twisted around extensions of the style, lobes about 2 mm in length and <1 mm in width, 14C in color.

*Ovaries*.—Inferior, triangular in cross section with angles unequally winged, about 1.2 cm in length and 9 mm in width (excluding wings), color is 144D to N34C merging to 47C at tips of the wings.

*Seed*.—Very numerous, ovoid in shape, 172C to 172D in color, <0.1 mm in length.

It is claimed:

1. A new and distinct cultivar of *Begonia* plant named 'YAMOUR' as herein illustrated and described.

* * * * *